United States Patent

Ide et al.

[11] Patent Number: 5,092,338
[45] Date of Patent: Mar. 3, 1992

[54] AUTOMATIC SPHYGMOMANOMETER

[75] Inventors: Tetsuya Ide; Hideo Hata, both of Fujinomiya, Japan

[73] Assignee: Terumo Corporation, Tokyo, Japan

[21] Appl. No.: 483,121

[22] Filed: Feb. 22, 1990

Related U.S. Application Data

[63] Continuation-in-part of Ser. No. 371,692, Jun. 21, 1989, abandoned, which is a continuation of Ser. No. 142,349, Dec. 28, 1987, abandoned, which is a continuation of Ser. No. 888,457, Jul. 21, 1986, abandoned.

[30] Foreign Application Priority Data

Jul. 25, 1985 [JP] Japan ............................ 60-112941[U]

[51] Int. Cl.$^5$ ................................................ A61B 5/02
[52] U.S. Cl. ..................................... 128/672; 128/677
[58] Field of Search ................ 128/672, 677, 680–686; 248/562, 636, 638

[56] References Cited

U.S. PATENT DOCUMENTS

| | | | |
|---|---|---|---|
| 3,405,288 | 10/1968 | Dittrich | 248/638 |
| 3,527,204 | 9/1970 | Lem | 128/686 |
| 3,905,353 | 9/1975 | Lichowsky | 128/677 |
| 4,088,126 | 5/1976 | Gemind | 128/677 |
| 4,328,810 | 5/1982 | Hill | 128/682 |
| 4,371,143 | 2/1983 | Ishida | 248/638 |
| 4,378,807 | 12/1980 | Peterson | 128/677 |
| 4,471,935 | 9/1984 | Chiba | 248/638 |
| 4,607,641 | 8/1986 | Fukushima | 128/680 |
| 4,646,754 | 3/1987 | Seale | 128/677 |
| 4,679,759 | 7/1987 | Ford | 248/562 |
| 4,768,925 | 9/1988 | Geupel | 248/638 |

*Primary Examiner*—Kyle L. Howell
*Assistant Examiner*—Robert L. Nasser, Jr.
*Attorney, Agent, or Firm*—Frishauf, Holtz, Goodman & Woodward

[57] ABSTRACT

An automatic sphygmomanometer is provided with an inflatable cuff adapted to be wrapped around an arm of a patient, instrument body for feeding compressed air into said cuff and for sensing blood pressure, a pump compartment having two end plates and pump disposed therein, a connecting tube which extends through an opening of the end plate of a pump compartment and which is formed of a soft silicone rubber, a seal for providing a noise seal between said connecting tube and the opening of the pump compartment. An elastomeric body is [shaped to receive said pump therein] rounded around the outer circumferential surface of said pump. The pump is accommodated within said compartment in a state where each end flat surface of said pump is exposed to a space which is defined between the end flat surface of the pump and an inner surface of the end plate of the pump compartment and a plurality of ribs which are formed on an inner circumferential surface of said elastomeric body, forming a gap between the inner circumferential surface of the pump compartment and the outer circumferential surface of said elastomeric body.

10 Claims, 3 Drawing Sheets

AUTOMATIC SPHYGMOMANOMETER

This application is a Continuation-In-Part of application Ser. No. 07/371,692 filed June 21, 1989, now abandoned, which is a continuation of application Ser. No. 07/142,349 filed Dec. 28, 1987, now abandoned, which is a continuation of application Ser. No. 06/888,457 filed July 21, 1986, now abandoned.

BACKGROUND OF THE INVENTION

This invention relates to an automatic sphygmomanometer having an internal pneumatic pump used in pressurizing a cuff wrapped around an arm of a patient when measuring blood pressure.

1. Field of the Invention

In conventional automatic sphygmomanometers having a pneumatic pump, the pump produces noise and vibration when operating. In hospital rooms where silence is required, the use of such a sphygmomanometer poses problems. In particular, it is normally desired that a patient be in a calm mental condition when undergoing a blood pressure measurement. This requires that care be taken to prevent noise and vibration that might otherwise agitate the patient.

To reduce vibration produced by the pneumatic pump during operation, a conventional approach is to support the pump by means such as a rubber vibration insulator. However, since the rubber vibration insulator is in mechanical contact with the pump and is itself mechanically joined to the case of the sphygmomanometer, pump vibration is diminished in dependence solely upon the damping factor of the rubber. In particular, since a sphygmomanometer has an overall weight of about 1 kg, it is not possible with the conventional arrangement to absorb the vibration energy because of the mass of the sphygmomanometer, and it is possible that the entire sphygmomanometer may resonate due to the vibration set up by the pump.

Another disadvantage with the conventional automatic sphygmomanometers is that measures for preventing leakage of noise produced by the pneumatic pump during operation are unsatisfactory. Since noise and vibration can cause anxiety in a patient undergoing a blood pressure measurement, the measured values of blood pressure are apt to be abnormal because of these external stimuli. This obviously is an unsatisfactory situation.

SUMMARY OF THE INVENTION

The present invention is contrived in the light of the above-mentioned circumstances and an object of the present invention is to provide an automatic sphygmomanometer adapted to prevent vibration and noise produced by a pneumatic pump from being transmitted to the exterior of the sphygmomanometer, thereby minimizing the adverse influence of such stimuli on blood pressure measurement.

According to the present invention, the foregoing object is attained by providing an automatic sphygmomanometer in which a compartment accommodating a pneumatic pump in its entirety is provided within the case of the automatic sphygmomanometer. The pneumatic pump is supported within the compartment by resilient means so as not to contact the walls of the compartment. The automatic sphygmomanometer further includes means for sealing the compartment.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

A preferred embodiment of an automatic sphygmomanometer according to the present invention will now be described in detail with reference to FIGS. 1 through 3.

Figure 1:
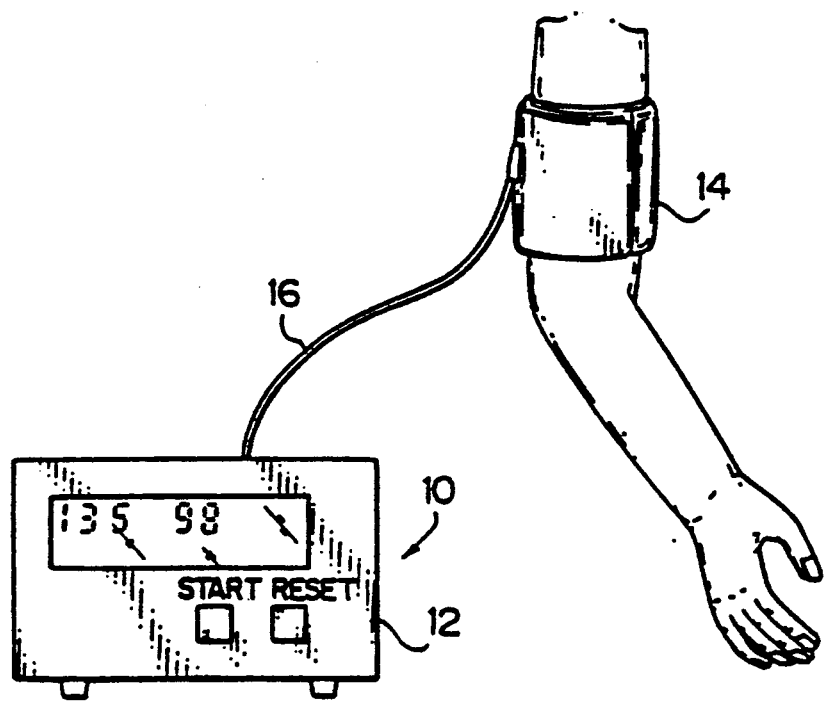
FIG. 1 is a perspective view schematically illustrating the arrangement of an embodiment of an automatic sphygmomanometer, which is equipped with a pneumatic pump, in accordance with the present invention.

With reference to FIG. 1, there is shown an embodiment of an automatic sphygmomanometer 10 comprising a sphygmomanometer instrument package 12, a cuff 14 wrapped around the arm of a patient and serving as a sensor for sensing the patient's blood pressure, and a pipe 16 connecting the instrument package 12 and the cuff 14.

The instrument package 12 is constituted by a detection system for detecting Korotkoff sounds, via the cuff 14, produced by the patient's blood vessels kept under pressure by the cuff, and for determining the patient's blood pressure from the applied pressure and the Korotkoff sounds.

Figure 3:
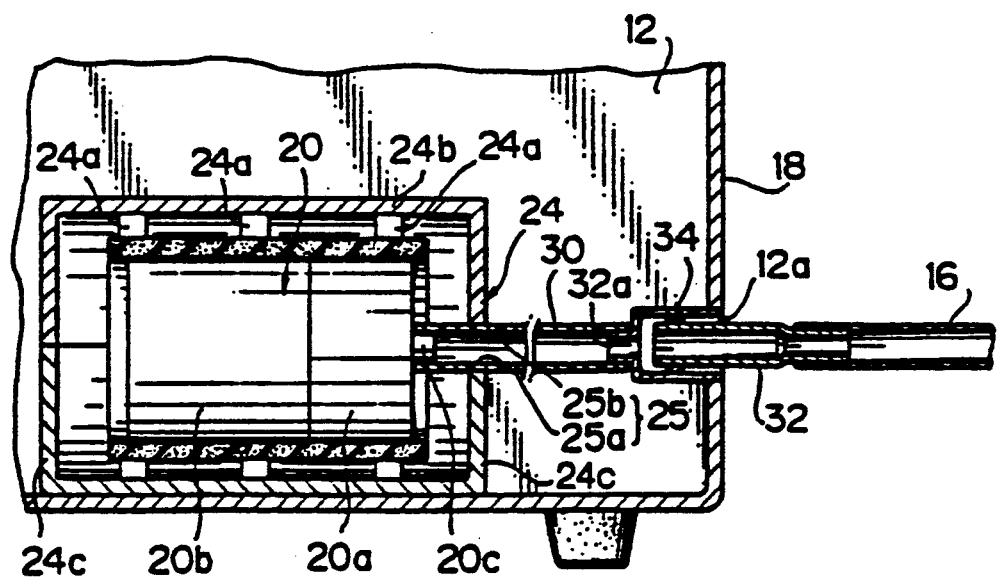
FIG. 3 is a sectional view illustrating the pneumatic pump accommodated in a compartment.
Figure 2:
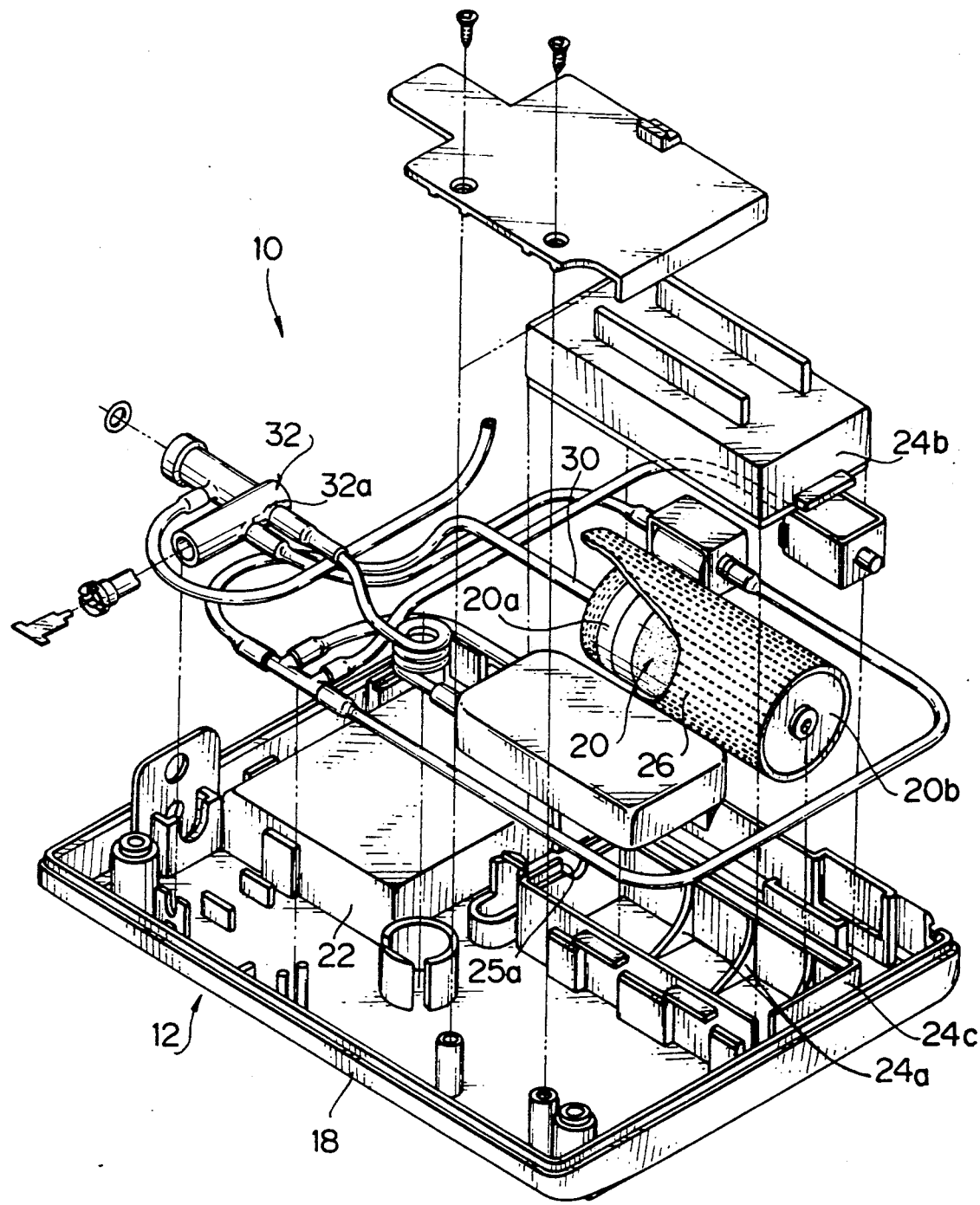
FIG. 2 is a sectional view schematically illustrating the manner in which the pneumatic pump is connected to tubing.

As shown in FIGS. 2 and 3, the sphygmomanometer instrument package 12 comprises a case 18, a pneumatic pump 20 disposed within the case 18 for feeding compressed air into the cuff 14 via the connecting pipe 16, and an arithmetic unit 22 for calculating blood pressure automatically from the Korotkoff sounds sensed by the cuff 14 and the pressure applied to the cuff 14.

More specifically, the case 18 is equipped with a compartment 24 sized to be larger than the pneumatic pump 20 for internally accommodating the same. The pneumatic pump 20 comprises a pump body 20a for emitting compressed air, and a motor 20b for driving the pump body 20a. The motor 20b drives an eccentric shaft, not shown, to move a diaphragm, not shown, up and down, thereby producing compressed air.

The pneumatic pump 20 is formed by a pump body 20a and a motor 20b each of which is arranged to be in the form of a cylindrical shape having the same diameter. An air output port 20c is formed at the substantially central portion of a flat side of the pneumatic pump 20. The pneumatic pump 20 is accommodated within a compartment 24 in such a manner that the entirety of the pneumatic pump 20 is covered by a vibration isolating and noise eliminating sheet 26 made of a resilient body. The vibration isolating and noise eliminating sheet 26 is made of a rubber foam which has, for example, a density of 15.8 kg/m³.

On the other hand, a plurality of support ribs 24a are integrally formed to project over the inner surface of the compartment 24 in the direction perpendicular to the longer axis of the pneumatic pump 20 which is arranged to be accommodated in the compartment 24. The inner surfaces of the support ribs 24a are respectively arranged to be circular in order to be capable of supporting the outer circumferential surface of the vibration isolating and noise eliminating sheet 26 wound around the pneumatic pump 20 and to thus prevent compartment 24 from coming into contact with the entirety of the outer circumferential surface of the vibration isolating and noise eliminating sheet 26. Thus, the vibration isolating and noise eliminating sheet 26 can be substantially separated from the inner surface of the compartment 24.

As a result, even if vibrations of the level which cannot be sealed by the vibration isolating and noise eliminating sheet 26 take place, the vibrations cannot be directly transmitted to the compartment 24, because of the space between the vibration isolating and noise eliminating sheet 26 and the compartment 24. Therefore, the energy of the vibrations is attenuated during transmission of the vibrations through such air in the space so that the vibrations transmitted to the compartment 24 are sufficiently weakened for the patient to ignore. Thus, according to this embodiment, a satisfactory vibration isolating effect can be obtained by arranging the structure in such a manner that the vibration isolating and noise eliminating sheet 26 is provided and the pneumatic pump 20 to which the vibration isolating and noise eliminating sheet 26 is wound is supported by the support ribs 24a.

The two end surfaces of the pneumatic pump 20 are contained within the space formed in the compartment 24. However, the outer circumferential surface of the pneumatic pump 20 is not completely enveloped by the vibration isolating and noise eliminating sheet 26. The pneumatic pump 20 has its two end surfaces projecting into the compartment 24 but not covered by sheet 26. As a result, the noise eliminating effect obtainable from the employment of the vibration isolating and noise eliminating sheet 26 is insufficient. Furthermore, the compartment 24 is constituted by a pair of bodies consisting of an upper half body 24b and a lower half body 24c which define a hollow and substantially rectangular parallelopiped when they are vertically coupled to each other. The surfaces of contact between the half bodies 24b and 24c, that is the upper surface of the lower half body 24c and the lower surface of the upper half body 24b, have corresponding semicircular recesses 25a and 25b which define a circular opening 25 when they are coupled to each other. The circular opening 25 through which a connecting tube 30 can pass is formed at the substantially central portion of an end surface of the compartment 24.

On the other hand, an end of the connecting tube 30 is, as shown in FIG. 3, connected to the air output port 20c formed in the pneumatic pump 20. The intermediate portion of the connecting tube 30 is taken out of the compartment 24 after it has passed through the opening 25, the other end portion of the connecting tube 30 being connected to a receiving member 32a of a connector 32. The connecting tube 30 is arranged to have an outer surface positioned in close contact with the inner surface of the opening 25. That is, the outer diameter of the connecting tube 30 and the inner diameter of the opening 25 are arranged to be substantially the same diameter. As a result of the design of the diameters and the fact that the connecting tube 30 is made of soft silicone rubber, noise seal means can be realized between the connecting tube 30 and the opening 25.

Thus, as a result of the provision of the noise seal means, although the compartment 24 must have the opening formed for the purpose of passing the connecting tube 30, the leakage of noise generated in the pneumatic pump 20 in the compartment 24 which cannot be prevented by the vibration isolating and noise eliminating sheet 26 wound around it can be assuredly prevented. Therefore, the patient which is subjected to the sphygmomanometry does not suffers from noise from the pneumatic pump 20. Thus, a static environment for the sphygmomanometry can be realized.

Thus, in accordance with the embodiment described above, the pneumatic pump 20, which is a source of both noise and vibration, is accommodated within the compartment 24 in a state wherein the outer circumferential surface of the pump 20 is surrounded by the vibration isolating and noise eliminating sheet 26, and a seal formed between the compartment 24 and the connecting tube 30. As a result, external transmission of the noise and vibration ascribable to the pneumatic pump 20 is surpressed.

Thus, in accordance with the embodiment described above, the pneumatic pump 20, which is a source of both noise and vibration, is accommodated within the compartment 24 in a state closely enveloped by the rubber foam body 26, and the compartment 24 is sealed. As a result, external transmission of the noise and vibration ascribable to the pneumatic pump 20 is suppressed.

The invention is not limited to the aforementioned embodiment but can be modified in various ways within the scope of the claims.

Figure 4:
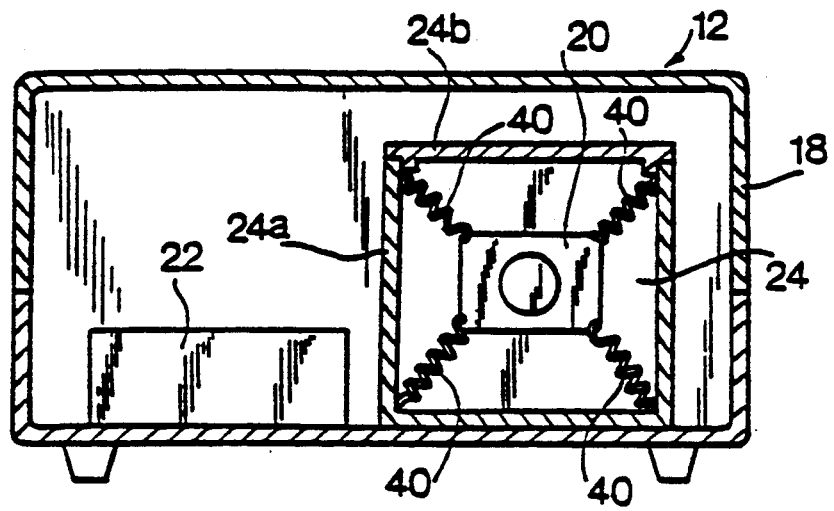
FIG. 4 is a sectional view of another embodiment illustrating how pump 20 is attached to compartment 24.

For example, though the resilient body is described above as being an rubber foam body, a sponge can also be used. An alternative modification is shown in FIG. 4, in which the resilient body comprises a plurality of coil springs. In this modification, each spring 40 has one end thereof attached to the inner wall of the compartment 24, and has its other end attached to the pump 20. Thus, the pneumatic pump 20 is suspended in a floating state within the space of the compartment 24 by means of the springs 40.

Figure 5:
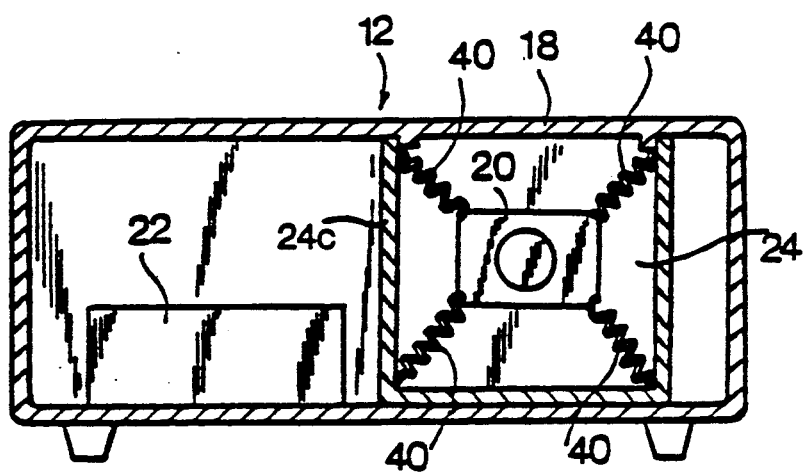
FIG. 5 is a sectional view of a further embodiment illustrating how pump 20 is attached to compartment 24.

Still another modification is illustrated in FIG. 5, in which the ceiling of the case 18 also serves as the lid of the compartment 24. In other words, the open top of the lower half 24c of compartment 24 is not closed by a separate lid, as shown by 24b in FIG 4. Instead, a portion of the case 18 serves to seal the compartment 24.

Since the automatic sphygmomanometer 10 of the invention prevents vibration and noise, the blood pressure detection system is well-suited for application to arrangements that rely upon detection of Korotkoff sounds. However, it goes without saying that the system is not limited to a Korotkoff sound detecting arrangement but can also be applied to a system in which blood pressure is sensed by oscillometry.

EFFECTS OF THE INVENTION

According to the present invention as described above, external noise and vibration produced by an automatic sphygmomanometer can be reduced or eliminated through a very simple construction.

As many apparently widely different embodiments of the present invention can be made without departing from the spirit and scope thereof, it is to be understood that the invention is not limited to the specific embodiments thereof except as defined in the appended claims.

What is claimed is:

1. An automatic sphygmomanometer, comprising:
   an inflatable cuff;
   instrument body means for feeding compressed air into said cuff and for sensing blood pressure, including a pump compartment, whereby said inflatable cuff is adapted to be wrapped around an arm of a patient and, when inflated, to compress a blood vessel in the arm around which it is wrapped;
   said pump compartment having two end plates and an opening formed in one of the end plates;
   a pump disposed within said compartment and having an outer circumferential surface and two substantially flat end surfaces;
   means for connecting said cuff and said instrument body means to one another including a connecting tube which extends through said opening in the one end plate of said pump compartment, said tube being formed of a resilient material, an outer surface of said connecting tube being sized to be in close contact with an inner surface of said opening to form a noise seal for preventing noise from escaping said pump compartment; and
   means for absorbing pump noise and vibration, provided between said pump and an inner surface of said compartment, and for supporting said pump such that said pump is spaced away from inner surfaces of said compartment, wherein said pump noise absorbing, vibration absorbing and pump supporting means comprises an elastomeric body surrounding the outer circumferential surface of said pump, said pump being accommodated within said compartment in a state such that the two flat end surfaces of said pump are spaced from an inner surface of the respective end plates of the pump compartment, and plurality of ribs spaced along an axial direction of said pump are positioned between a circumferential surface of said elastomeric body and said pump compartment forming a plurality of gaps spaced along said axial direction each of which is defined by an inner surface of the pump compartment, an outer surface of said elastomeric body, and at least one of said ribs; and
   wherein said pump includes means for generating compressed air for supply to said cuff via the connecting means while said pump is positioned in said state.

2. The automatic sphygmomanometer according to claim 1, wherein said elastomeric body has a cavity for snugly holding said pump, said pump being accommodated within said compartment in a state where said pump is snugly enclosed within said elastomeric body.

3. The automatic sphygmomanometer according to claim 2, wherein said elastomeric body consists of a rubber foam.

4. The automatic sphygmomanometer according to claim 2, wherein said elastomeric body consists of sponge.

5. The automatic sphygmomanometer according to claim 1, wherein said compartment is comprised of a box open on top, and an openable lid closing the open top of said box.

6. The automatic sphygmomanometer according to claim 5, wherein said lid comprises a discrete member.

7. The automatic sphygmomanometer according to claim 5, wherein said compartment is disposed within a case.

8. The automatic sphygmomanometer of claim 1, wherein said pump compartment is comprised of a pair of compartment halves which are divided into upper and lower ones through a horizontal plane, and which are in contact with each other at the under surface of the upper compartment half and the upper surface of the lower compartment half.

9. The automatic sphygmomanometer according to claim 8, wherein said opening is constituted by a pair of opening halves which are formed on the under surface of the upper compartment half and the upper surface of the lower compartment half, respectively.

10. The automatic sphygmomanometer according to claim 9, wherein said opening is defined by a circumferential surface.

* * * * *

UNITED STATES PATENT AND TRADEMARK OFFICE
CERTIFICATE OF CORRECTION

PATENT NO. : 5,092,338
DATED : March 3, 1992
INVENTOR(S) : IDE et al

It is certified that error appears in the above-identified patent and that said Letters Patent is hereby corrected as shown below:

Column 1, line 11, below "BACKGROUND OF THE INVENTION", insert --Field of the Invention--.

Column 1, line 16, replace "1. Field of the Invention" with --Description of the Prior Art--.

Column 3, line 26, replace "such air in the" with --the air in such--.

Column 5, line 41 (claim 1), before "plurality", insert --a--.

Signed and Sealed this

Tenth Day of August, 1993

Attest:

MICHAEL K. KIRK

Attesting Officer  Acting Commissioner of Patents and Trademarks